(12) United States Patent
Sakuma et al.

(10) Patent No.: US 11,717,817 B2
(45) Date of Patent: Aug. 8, 2023

(54) DISPENSING APPARATUS, LIQUID DISPENSING METHOD, AND CELL DISPENSING METHOD

(71) Applicant: NATIONAL UNIVERSITY CORPORATION KYUSHU UNIVERSITY, Fukuoka (JP)

(72) Inventors: Shinya Sakuma, Nagoya (JP); Yusuke Kasai, Nagoya (JP); Fumihito Arai, Nagoya (JP)

(73) Assignee: NATIONAL UNIVERSITY CORPORATION KYUSHU UNIVERSITY

( * ) Notice: Subject to any disclaimer, the term of this patent is extended or adjusted under 35 U.S.C. 154(b) by 699 days.

(21) Appl. No.: 16/624,456

(22) PCT Filed: Jun. 19, 2018

(86) PCT No.: PCT/JP2018/023242
§ 371 (c)(1),
(2) Date: Dec. 19, 2019

(87) PCT Pub. No.: WO2018/235804
PCT Pub. Date: Dec. 27, 2018

(65) Prior Publication Data
US 2020/0179918 A1 Jun. 11, 2020

(30) Foreign Application Priority Data

Jun. 19, 2017 (JP) .................................. 2017-119895

(51) Int. Cl.
*B01L 3/02* (2006.01)
*C12M 1/26* (2006.01)

(52) U.S. Cl.
CPC .......... *B01L 3/0237* (2013.01); *C12M 33/04* (2013.01); *B01L 2300/0832* (2013.01); *B01L 2300/123* (2013.01)

(58) Field of Classification Search
CPC ...................................... B05B 1/086
See application file for complete search history.

(56) References Cited

U.S. PATENT DOCUMENTS

| 2001/0016358 | A1 | 8/2001 | Osawa et al. | |
| 2010/0102093 | A1* | 4/2010 | Ham .................. | B05B 1/086 239/102.2 |
| 2013/0309144 | A1* | 11/2013 | Yu .................... | B01L 3/0275 422/525 |

FOREIGN PATENT DOCUMENTS

| JP | S46-6098 A | 6/1971 |
| JP | S56-31650 A | 3/1981 |

(Continued)

OTHER PUBLICATIONS

Jun. 7, 2022 Office Action issued in Japanese Application No. 2019-525621.

(Continued)

*Primary Examiner* — Elizabeth A Robinson
*Assistant Examiner* — Ryan J Dowty
(74) *Attorney, Agent, or Firm* — Oliff PLC

(57) ABSTRACT

A dispensing apparatus, a liquid dispensing method, and a cell dispensing method which can dispense liquid with very high accuracy. A dispensing apparatus includes a glass pipette, a tubular elastic member, a rod-shaped member, and a piezoelectric element actuator. A portion of the tubular elastic member located adjacent to a first open end thereof covers a portion of the glass pipette located adjacent to an opening portion thereof. A portion of the tubular elastic member located adjacent to a second open end thereof covers at least a forward end portion of the rod-shaped (Continued)

member. When the piezoelectric element actuator pushes the rod-shaped member toward the opening portion of the glass pipette, the tubular elastic member deforms such that the volume of the internal space of the tubular elastic member decreases.

8 Claims, 6 Drawing Sheets

(56) References Cited

FOREIGN PATENT DOCUMENTS

| | | |
|---|---|---|
| JP | 2001-228060 A | 8/2001 |
| JP | 2014-92427 A | 5/2014 |

OTHER PUBLICATIONS

Aug. 7, 2018 International Search Report issued in International Patent Application No. PCT/JP2018/023242.

* cited by examiner

US 11,717,817 B2

DISPENSING APPARATUS, LIQUID DISPENSING METHOD, AND CELL DISPENSING METHOD

TECHNICAL FIELD

The technical field of the present specification relates to a dispensing apparatus, a liquid dispensing method, and a cell dispensing method.

BACKGROUND ART

A dispensing apparatus is used for suppling a sample or a reagent to wells. In order to perform accurate measurement, it is preferred that the dispensing apparatus can dispense liquid accurately. Therefore, dispensing apparatuses which can perform accurate dispensing have been developed.

For example, Patent Document 1 discloses a dispensing apparatus which includes a pipette, a piston, and a piezoelectric actuator. This dispensing apparatus can cause a liquid droplet to fly directly to the bottom of a container. Therefore, this dispensing apparatus eliminates the necessity of a tip-touch operation and a tip-down operation. Also, this dispensing apparatus can dispense liquid in an amount as small as 1 µL.

PRIOR ART DOCUMENT

Patent Document

Patent Document 1: Japanese Patent Application Laid-Open (kokai) No. 2001-228060

SUMMARY OF THE INVENTION

Problem to be Solved by the Invention

Incidentally, in the case of an experiment performed on cells or the like, the cells may be dispensed to wells in such a manner that one cell is dispensed to each well. In the case where cells are dispensed one by one, a dispensing apparatus used in the experiment is required to dispense liquid in an amount of 1 nL or less. Although the liquid dispensing amount varies depending on the type of cells, the dispensing apparatus dispenses the liquid in an amount of, for example, 10 pL. For such liquid dispensing operation, the dispensing apparatus must have very high accuracy.

Also, in actuality, the operation of dispensing cells one by one is very difficult. Conventionally, the dispensing apparatus must repeat many times a collecting operation and a releasing operation until the dispensing apparatus succeeds in taking out one cell from a culture solution containing a large number of cells. In such circumstances, an enormous amount of time is needed to supply cells to wells during the experiment in such a manner that one cell is supplied to each well.

The technique of the present specification has been accomplished so as to solve the problem of the above-described conventional technique. Namely, its object is to provide a dispensing apparatus, a liquid dispensing method, and a cell dispensing method which can dispense liquid with very high accuracy.

Means for Solving the Problem

A dispensing apparatus according to a first aspect includes a dispensing spout, a tubular member which is connected to the dispensing spout and which is elastically deformable, and an actuator for compressing the tubular member in an axial direction of the tubular member. The tubular member elastically deforms in the axial direction in its elastically deformable region.

In this dispensing apparatus, the tubular member elastically deforms in the axial direction in its elastically deformable region. Namely, the tubular member deforms in accordance with the displacement amount of the actuator. As a result of the compression, the volume of the internal space of the tubular member decreases. Accordingly, an approximately directly proportional relation holds between the voltage applied to the actuator and the amount of released liquid. Therefore, a dispensing apparatus which dispenses liquid with very high accuracy is realized. Also, this dispensing apparatus can dispense one cell in a culture solution to a well without fail.

Effect of the Invention

The present specification provides a dispensing apparatus, a liquid dispensing method, and a cell dispensing method which can dispense liquid with very high accuracy.

MODES FOR CARRYING OUT THE INVENTION

Specific embodiments will now be described with reference to the drawings, with a dispensing apparatus, a liquid dispensing method, and a cell dispensing method being used as examples.

First Embodiment

1. Dispensing Apparatus

Figure 1:
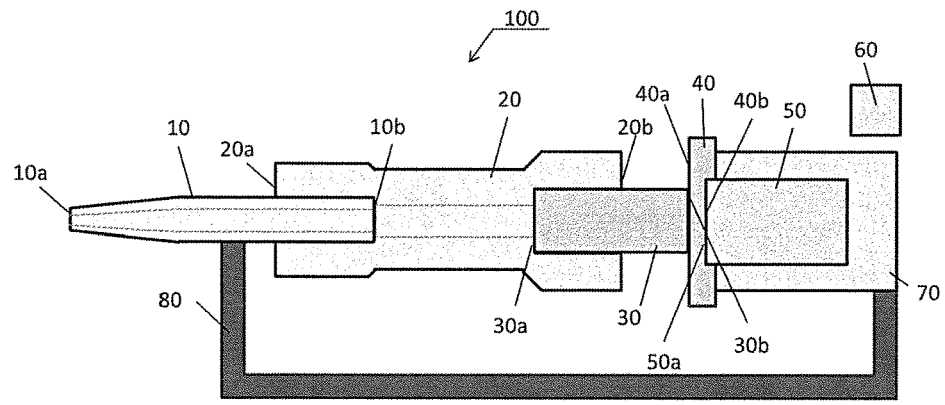
FIG. 1 View schematically showing the structure of a dispensing apparatus of a first embodiment.

FIG. 1 is a view schematically showing the structure of a dispensing apparatus 100 of the present embodiment. As shown in FIG. 1, the dispensing apparatus 100 includes a glass pipette 10, a tubular elastic member 20, a rod-shaped member 30, a plate spring 40, a piezoelectric element actuator 50, a control unit 60, a housing 70, and a fixing member 80.

The glass pipette 10 is a dispensing member for containing a liquid to be dispensed. The glass pipette 10 is fixed to the main body of the dispensing apparatus 100. The glass pipette 10 has a cylindrical shape. The glass pipette 10 has a dispensing spout 10a and an opening portion 10b. The dispensing spout 10a is an opening portion through which the liquid is injected into the internal space of the glass pipette 10 and is released from the glass pipette 10. The opening portion 10b is located on a side opposite the dispensing spout 10a. The opening portion 10b is fitted into the tubular elastic member 20. Specifically, the opening portion 10b of the glass pipette 10 is covered with a portion of the tubular elastic member 20, which portion is located adjacent to a first open end 20a thereof. As a matter of course, the material of the glass pipette 10 is glass.

The tubular elastic member 20 is an elastic member having a cylindrical shape. The tubular elastic member 20 is a tubular member which is connected to the dispensing spout 10a and elastically deforms. The tubular elastic member 20 is a connection member for connecting the glass pipette 10 and the rod-shaped member 30. Therefore, the tubular elastic member 20 is connected to the glass pipette 10 and the rod-shaped member 30. The tubular elastic member 20 has the first open end 20a and a second open end 20b. A portion of the tubular elastic member 20 located adjacent to the first open end 20a covers a portion of the glass pipette 10 located adjacent to the opening portion 10b. A portion of the tubular elastic member 20 located adjacent to the second open end 20b covers at least a forward end portion of the rod-shaped member 30. Namely, a first end portion 30a of the rod-shaped member 30 is fitted into the interior space of the second open end 20b of the tubular elastic member 20. The material of the tubular elastic member 20 is resin. An example of resin is silicone resin.

The rod-shaped member 30 is connected to the inner wall of the tubular elastic member 20. Specifically, the rod-shaped member 30 is inserted into the tubular elastic member 20. The rod-shaped member 30 has a second end portion 30b as well as the above-mentioned first end portion 30a. The first end portion 30a is a forward end portion of the rod-shaped member 30. The second end portion 30b is an end portion located on the side opposite the first end portion 30a. The rod-shaped member 30 moves in the axial direction of the tubular elastic member 20. The first end portion 30a of the rod-shaped member 30 is inserted into the tubular elastic member 20 from the second open end 20b side. The second end portion 30b is fixed to the plate spring 40. The space inside the glass pipette 10, the space inside the tubular elastic member 20, and the first end portion of the rod-shaped member 30 define a cavity. This cavity can store liquid, etc. The material of the rod-shaped member 30 is metal. The material of the rod-shaped member 30 may be any of other solid materials such hard resin.

The plate spring 40 is disposed at a position between piezoelectric element actuator 50 and the rod-shaped member 30. The plate spring 40 is disposed at a position between the piezoelectric element actuator 50 and the tubular elastic member 20. The plate spring 40 has a first surface 40a and a second surface 40b. The first surface 40a is in contact with the second end portion 30b of the rod-shaped member 30. The second surface 40b is in contact with a first surface 50a of the piezoelectric element actuator 50.

The piezoelectric element actuator 50 is an actuator for reciprocating the rod-shaped member 30 in the axial direction of the tubular elastic member 20. The piezoelectric element actuator 50 compresses the tubular elastic member 20 in the axial direction of the tubular elastic member 20. The piezoelectric element actuator 50 reciprocates the rod-shaped member 30 in the axial direction of the rod-shaped member 30. The piezoelectric element actuator 50 has a first end portion 50a. The first end portion 50a of the piezoelectric element actuator 50 is in contact with the second surface 40b of the plate spring 40.

The control unit 60 controls an application voltage applied to the piezoelectric element actuator 50. For example, the control unit 60 applies a positive voltage to the piezoelectric element actuator 50. In this case, the piezoelectric element actuator 50 pushes the rod-shaped member 30 toward the glass pipette 10. Also, the control unit 60 applies a negative voltage to the piezoelectric element actuator 50. In this case, the piezoelectric element actuator 50 pulls the rod-shaped member 30 toward the side opposite the glass pipette 10. Thus, the piezoelectric element actuator 50 produces a reciprocating motion in the axial direction of the glass pipette 10. As a result, the rod-shaped member 30 reciprocates in the axial direction of the glass pipette 10.

The housing 70 is the main body of the dispensing apparatus 100. The fixing member 80 is used to fix a predetermined portion of the glass pipette 10 to the housing 70.

2. Sizes of Respective Portions

The outer diameter of the glass pipette 10 on the opening portion 10b side is greater than the inner diameter of the tubular elastic member 20. Therefore, a portion of the tubular elastic member 20 located adjacent to the first open end 20a is deformed to cover the glass pipette 10. Namely, the inner wall of the tubular elastic member 20 is expanded. The outer diameter of the first end portion 30a of the rod-shaped member 30 is greater than the inner diameter of the tubular elastic member 20. Therefore, a portion of the tubular elastic member 20 located adjacent to the second open end 20b is deformed to cover the rod-shaped member 30. Namely, the inner wall of the tubular elastic member 20 is expanded.

When the rod-shaped member 30 is pushed toward the tubular elastic member 20, the rod-shaped member 30 contracts the tubular elastic member 20. As a result of this stress, the tubular elastic member 20 deforms as described later. At that time, the glass pipette 10 and the rod-shaped member 30 do not slide in relation to the inner wall of the tubular elastic member 20. The outer diameter of the rod-shaped member 30 is greater than the inner diameter of the glass pipette 10. During the reciprocating motion of the rod-shaped member 30 produced by the piezoelectric element actuator 50, the rod-shaped member 30 does not come into contact with the glass pipette 10. Therefore, there is no possibility that the rod-shaped member 30 and the glass pipette 10 interfere with each other.

The outer diameter of the cylindrical glass pipette 10 is 0.8 mm to 1.2 mm. The inner diameter of the cylindrical tubular elastic member 20 is 0.6 mm to 1.0 mm. The outer diameter of the cylindrical rod-shaped member 30 is 1.2 mm to 2.0 mm. These diameters are approximate values and may fall within respective numerical ranges different from the above-described numerical ranges.

3. Action of Tubular Elastic Member

Figure 2:
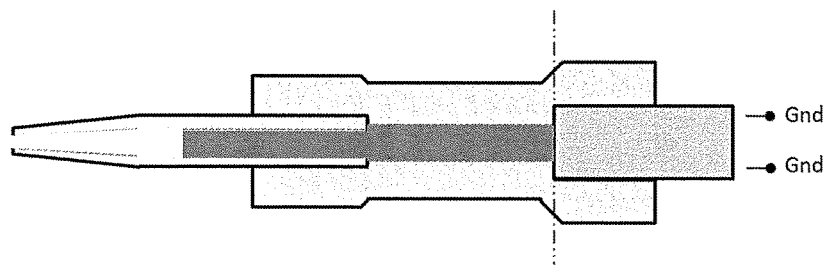
FIG. 2 First view showing operation of the dispensing apparatus of the first embodiment.

FIG. 2 is a first view showing the operation of the dispensing apparatus 100 of the present embodiment. The voltage applied to the piezoelectric element actuator 50 is zero. Therefore, the rod-shaped member 30 is located at a reference position.

Figure 3:
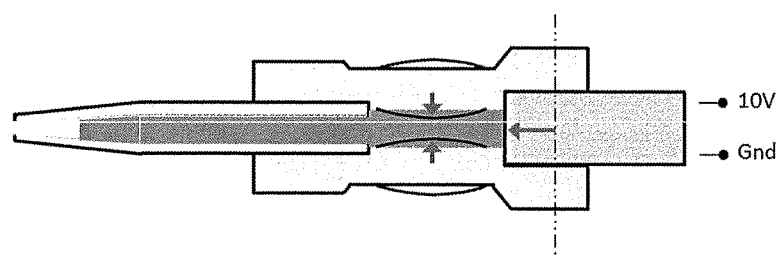
FIG. 3 Second view showing the operation of the dispensing apparatus of the first embodiment.

FIG. 3 is a second view showing the operation of the dispensing apparatus 100 of the present embodiment. The voltage applied to the piezoelectric element actuator 50 assumes a positive value. For example, the voltage is 10 V. In this case, the rod-shaped member 30 advances toward the opening portion 10b of the glass pipette 10. As a result, the liquid within the liquid containing space formed by the glass pipette 10 and the tubular elastic member 20 moves toward the dispensing spout 10a.

As shown in FIG. 3, when the piezoelectric element actuator 50 pushes the rod-shaped member 30 toward the opening portion 10b of the glass pipette 10, the tubular elastic member 20 elastically deforms such that the volume of the internal space of the tubular elastic member 20 decreases. Namely, in the case where the piezoelectric element actuator 50 pushes the tubular elastic member 20 from the second open end 20b side toward the first open end 20a of the tubular elastic member 20, the tubular elastic member 20 elastically deforms such that the volume of the internal space of the tubular elastic member 20 decreases. At that time, the tubular elastic member 20 shrinks in the axial direction. Namely, the tubular elastic member 20 contracts.

4. Effect of Present Embodiment

Despite the deformation of the tubular elastic member 20, no gap is formed between the inner surface of the tubular elastic member 20 and the outer surface of the glass pipette 10. Similarly, no gap is formed between the inner surface of the tubular elastic member 20 and the outer surface of the rod-shaped member 30. Accordingly, the release amount of the liquid released from the dispensing spout 10a is approximately proportional to the application voltage applied to the piezoelectric element actuator 50. Namely, this dispensing apparatus 100 can perform accurate liquid dispensing.

Also, at a certain degree of deformation, the tubular elastic member 20 slightly deforms such that the cross-sectional area of the internal space of at least portion of the tubular elastic member 20 decreases. At that time, the cross-sectional area of at least portion of the internal space of the tubular elastic member 20 is slightly smaller than the cross-sectional area of the internal space of the tubular elastic member 20 in an ordinary state. Namely, the tubular elastic member 20 is slightly concaved. Even in such a case, the dispensing apparatus 100 can perform liquid dispensing with a sufficiently high accuracy.

Notably, in the case where the wall thickness of the tubular elastic member 20 is small, the tubular elastic member 20 deforms such that the cross-sectional area of the internal space of at least portion of the tubular elastic member 20 increases. In such a case, a gap is more likely to be formed between the inner surface of the tubular elastic member 20 and the outer surface of the glass pipette 10. Also, a gap is more likely to be formed between the inner surface of the tubular elastic member 20 and the outer surface of the rod-shaped member 30. In this case, when the rod-shaped member 30 is pushed by the piezoelectric element actuator 50, the liquid escapes to these gaps. Accordingly, the release amount of the liquid released from the dispensing spout 10a does not have a proportional relation to the application voltage applied to the piezoelectric element actuator 50. Therefore, the tubular elastic member 20 preferably has a sufficiently large wall thickness.

As described above, this dispensing apparatus 100 can dispense the liquid in an amount approximately proportional to the application voltage of the piezoelectric element actuator 50 set by the control unit 60. For example, the dispensing apparatus 100 can dispense the liquid in an amount as small as 10 pL with high accuracy as will be described later.

In this dispensing apparatus 100, the tubular elastic member 20 elastically deforms in its elastically deformable region. Thus, the tubular elastic member 20 elastically deforms in the axial direction of the tubular elastic member 20.

5. Modifications

5-1. Dispensing Member

The dispensing member of the present embodiment is the glass pipette 10. However, the material of the dispensing member is not limited to glass and may be a resin such as acrylic resin or a metal. The dispensing member may be a tubular member having a bent portion. The inner diameter of the dispensing member may decrease toward the dispensing spout.

5-2. Pump

Figure 4:
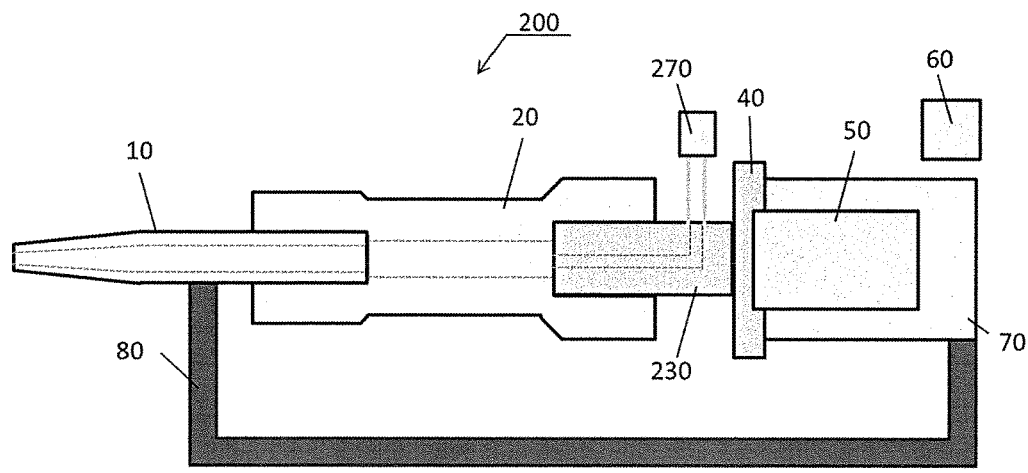
FIG. 4 View schematically showing the structure of a dispensing apparatus in a modification of the first embodiment.

FIG. 4 is a view schematically showing the structure of a dispensing apparatus 200 in a modification of the present embodiment. As shown in FIG. 4, the dispensing apparatus 200 includes a rod-shaped member 230 having a through hole, and a pump 270 for feeding a liquid to the through hole.

5-3. Plate Spring and Piezoelectric Element Actuator

The plate spring 40 may be omitted in some cases. In such a case, the rod-shaped member 30 is provided on the piezoelectric element actuator 50. Alternatively, the piezoelectric element actuator 50 itself may play the role of the rod-shaped member 30.

5-4. Combination

The above-described modifications may be combined freely.

6. Summary of Present Embodiment

As having been described above, the dispensing apparatus 100 of the present embodiment includes the glass pipette 10, the tubular elastic member 20, the rod-shaped member 30, the piezoelectric element actuator 50, and the control unit 60. The tubular elastic member 20 deforms in accordance with the motion of the rod-shaped member 30. Therefore, the dispensing apparatus 100 can dispense a minute volume of liquid.

Second Embodiment

A second embodiment will be described. The second embodiment is a method of dispensing liquid containing cells, etc. For description, the dispensing apparatus 100 of the first embodiment is used. However, a dispensing apparatus other than the dispensing apparatus 100 of the first embodiment may be used. However, it is preferred for the dispensing method of the present embodiment to use the dispensing apparatus 100 of the first embodiment.

1. Cell Dispensing Method

This cell dispensing method comprises a first liquid injecting step of injecting a first liquid into the internal space of the glass pipette 10; a gas injecting step of injecting a gas into the internal space of the glass pipette 10; a cell collecting step of collecting only one of cells contained in a second liquid while injecting the second liquid into the internal space of the glass pipette 10; and a releasing step of releasing the second liquid and the cell from the glass pipette 10 into a container.

1-1. First Liquid Injecting Step

Figure 5:
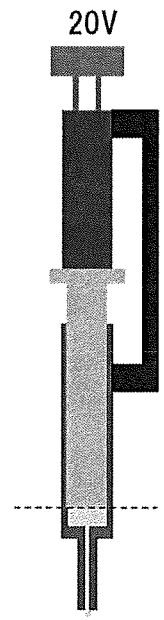
FIG. 5 First view used for describing a cell dispensing method in a second embodiment.

As shown in FIG. 5, the first liquid is injected into the internal space of the glass pipette 10 of the dispensing apparatus 100. The first liquid is not a liquid to be dispensed.

1-2. Gas Injecting Step

Figure 6:
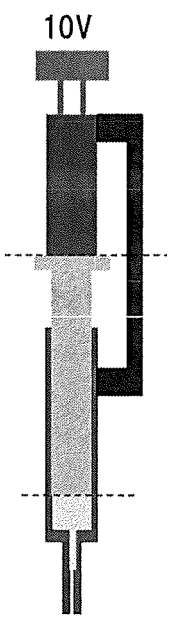
FIG. 6 Second view used for describing the cell dispensing method in the second embodiment.

As shown in FIG. 6, after the injection of the first liquid, the gas is injected into the internal space of the glass pipette 10. The gas is, for example, air. As a result, the first liquid is confined in an inner part of the dispensing apparatus 100.

1-3. Second Liquid Injecting Step (Cell Collecting Step)

Figure 7:
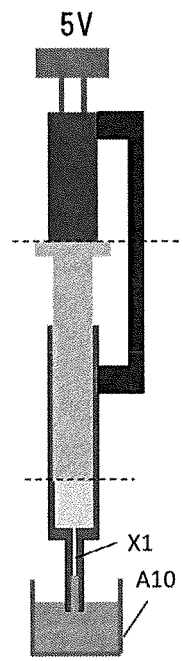
FIG. 7 Third view used for describing the cell dispensing method in the second embodiment.

As shown in FIG. 7, after the injection of the gas, only one of the cells contained in the second liquid is collected, while the second liquid is being injected from a container A10. The second liquid is the liquid to be dispensed. In this stage, a separation bubble X1 is generated between the first liquid and the second liquid. The second liquid within the container A10 contains a plurality of cells. The dispensing apparatus 100 can easily collect only one cell among the plurality of cells.

As described above, the control unit 60 of the dispensing apparatus 100 controls the application voltage such that the first liquid is held on the side toward the tubular elastic member 20, the second liquid is held on the side toward the dispensing spout 10a, and the separation bubble is generated between the first liquid and the second liquid.

1-4. Releasing Step

Figure 8:
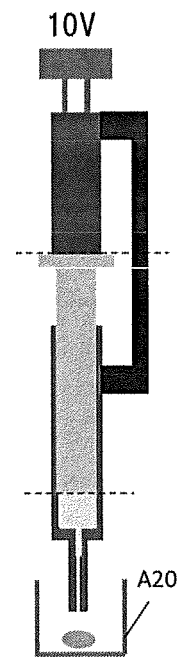
FIG. 8 Fourth view used for describing the cell dispensing method in the second embodiment.

As shown in FIG. 8, the second liquid and the cell are released from the glass pipette 10 into a container A20 located outside the dispensing apparatus 100. As a result, the second liquid and the single cell are supplied to the container A20.

As described above, the control unit 60 controls the application voltage such that the first liquid is held on the side toward the tubular elastic member 20, the second liquid is held on the side toward the dispensing spout 10a, and the separation bubble is generated between the first liquid and the second liquid.

2. Effect of Present Embodiment

In the present embodiment, the separation bubble X1 is generated in the glass pipette 10. The separation bubble X1 has a role of separating the first liquid and the second liquid from each other, thereby preventing the liquids from mixing. Also, the separation bubble X1 has a role of a shield for preventing active cells from the second liquid to the first liquid.

3. Modifications

3-1. Liquid Dispensing Method

In the present embodiment, one of a large number of cells contained in the second liquid is dispensed. However, only the liquid may be dispensed without dispensing cells. In such a case, in the second liquid injecting step, the second liquid is injected into the internal space of the glass pipette 10 after the injection of the gas. In this stage, the separation bubble X1 is generated between the first liquid and the second liquid. In the releasing step, the second liquid is released from the glass pipette 10 into the container A10, and a portion of the separation bubble X1 is released.

Since the separation bubble X1 is partially released, the second liquid can be released completely without fail. Therefore, the second liquid and the cell do not remain in the glass pipette 10 and the tubular elastic member 20. Notably, there is no possibility that the dispensing apparatus 100 releases the first liquid into the container A10.

3-2. Plurality of Separation Bubbles

Two separation bubbles X1 may be generated in the glass pipette 10 and the tubular elastic member 20. For generation of two separation bubbles X1, the gas injecting step and the liquid injecting step are repeated. Namely, the gas is injected after the second liquid injecting step. Subsequently, a third liquid and another cell are collected. In this stage, a single cell is held by each of the second liquid and the third liquid separated by the separation bubble X1. Therefore, two cells can be dispensed continuously by successively releasing the third liquid and the second liquid. The above-mentioned method can be applied to the case where three or more cells are to be dispensed.

3-3. Dispensing Unit

A dispensing unit may be used so as to carry out this cell dispensing method. This dispensing unit includes, for example, the dispensing apparatus 100 of the first embodiment; a drive unit for moving the dispensing apparatus 100 in an X axial direction, a Y axial direction, and a Z axial direction; a drive control unit for controlling the drive unit; and a sensor for capturing cells in the second liquid.

3-4. Combination

The above-described modifications may be combined freely.

4. Summary of Present Embodiment

In the present embodiment, the separation bubble X1 appropriately separates the first liquid and the second liquid from each other. Therefore, the cells contained in the second liquid do not escape to the first liquid. Therefore, it is possible to supply the second liquid and cells to wells in such a manner that, for example, one cell is supplied to each well.

Third Embodiment

A third embodiment will be described. The dispensing apparatus 100 of the first embodiment has the tubular elastic member 20. However, even a material other than the material of the tubular elastic member 20 elastically deforms in its elastically deformable region. For example, glass elastically deforms, although its deformation is slight, in a region in which the glass can elastically deform without exceeding its yield point. In general, glass does not easily deform. Therefore, glass can be used in the case where a small amount of liquid is dispensed.

1. Dispensing Apparatus

Figure 9:
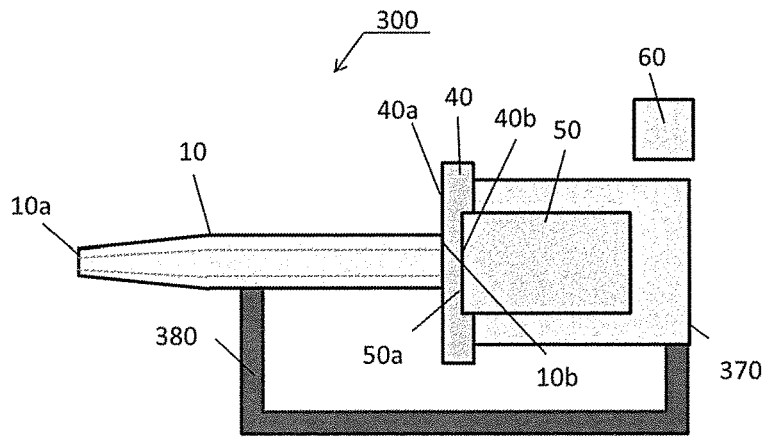
FIG. 9 View schematically showing the structure of a dispensing apparatus of a third embodiment.

FIG. 9 is a view schematically showing the structure of a dispensing apparatus 300 of the present embodiment. As shown in FIG. 9, the dispensing apparatus 300 includes the glass pipette 10, the plate spring 40, the piezoelectric element actuator 50, the control unit 60, a housing 370, and a fixing member 380.

The housing 370 is the main body of the dispensing apparatus 300. The fixing member 380 is used to fix a predetermined portion of the glass pipette 10 to the housing 370.

The glass pipette 10 is a tubular member having the dispensing spout 10a and the opening portion 10b. The glass pipette 10 elastically deforms in the axial direction of the tubular glass pipette 10 in its elastically deformable region. The glass pipette 10 is a unitary glass member having the dispensing spout 10a. The plate spring 40 has the first surface 40a and the second surface 40b. The opening portion 10b of the glass pipette 10 is joined to the first surface 40a of the plate spring 40. For example, an adhesive or the like is used for such joining.

2. Operation of Dispensing Apparatus

When a predetermined voltage is applied to the piezoelectric element actuator 50, the piezoelectric element actuator 50 presses the glass pipette 10 in the axial direction thereof. Therefore, the distance between the opening portion 10b and the fixing member 380 measured along the glass pipette 10 decreases slightly. Namely, the glass pipette 10 elastically deforms in its axial direction in the elastically deformable region. As will be described later, the compression amount is approximately proportional to the application voltage of the piezoelectric element actuator 50. As a result of the compression, the volume of the internal space of the glass pipette 10 decreases. Thus, a small amount of liquid is dispensed.

3. Effect of Present Embodiment

Although the glass pipette 10 of the present embodiment does not easily deform, the glass pipette 10 elastically deforms in its elastically deformable region. Therefore, the glass pipette 10 elastically deforms by a slight amount in proportion to the input voltage. Accordingly, the dispensing apparatus 300 of the present embodiment is suitable for applications in which a small amount of liquid is dispensed.

Experiments

1. Relation Between Application Voltage and Liquid Release Amount

The relation between the application voltage applied to the piezoelectric element actuator 50 and the release amount of the liquid released from the dispensing spout 10a was investigated by using the dispensing apparatus 100 of the first embodiment.

Figure 10:
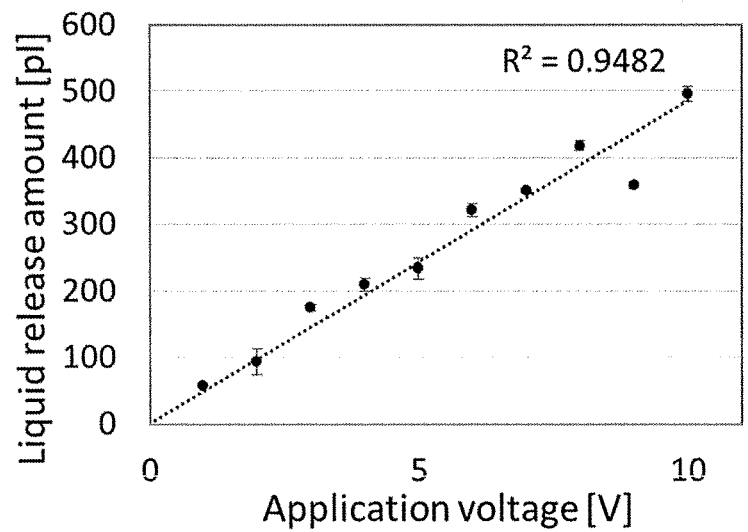
FIG. 10 Graph showing the relation between application voltage and liquid release amount in the dispensing apparatus of the first embodiment.

FIG. 10 is a first graph showing the relation between the application voltage and the liquid release amount. As shown in FIG. 10, an approximately proportional relation is present between the application voltage and the liquid release amount. Therefore, the dispensing operation can be performed accurately by inputting an appropriate application voltage to the piezoelectric element actuator 50.

Also, as shown in FIG. 10, the approximately proportional relation is present between the application voltage and the liquid release amount even when the liquid dispensing amount is 1 nL or less. Therefore, the dispensing apparatus 100 can dispense the liquid in an amount as small as 10 pL with high accuracy.

Next, the relation between the application voltage applied to the piezoelectric element actuator 50 and the release amount of the liquid released from the dispensing spout 10a was investigated by using the dispensing apparatus 300 of the third embodiment.

Figure 11:
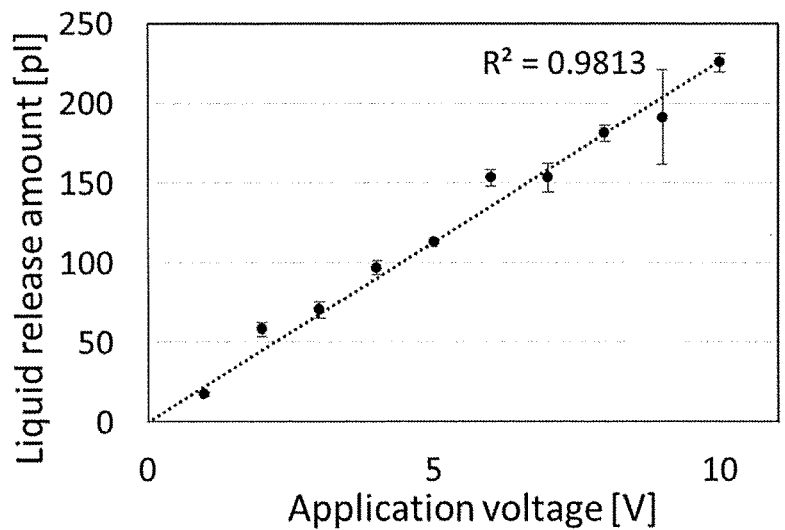
FIG. 11 Graph showing the relation between application voltage and liquid release amount in the dispensing apparatus of the third embodiment.

FIG. 11 is a second graph showing the relation between the application voltage and the liquid release amount. As shown in FIG. 11, an approximately proportional relation is present between the application voltage and the liquid release amount. Therefore, the dispensing operation can be performed accurately by inputting an appropriate application voltage to the piezoelectric element actuator 50.

Also, as shown in FIG. 11, the approximately proportional relation is present between the application voltage and the liquid release amount even when the liquid dispensing amount is 1 nL or less. Therefore, the dispensing apparatus 300 can dispense the liquid in an amount as small as 10 pL with high accuracy.

Notably, the compression portion (glass pipette 10) of the dispensing apparatus 300 of the third embodiment is smaller in elastic deformation than the compression portion (tubular elastic member 20) of the dispensing apparatus 100 of the first embodiment. Therefore, when the same input voltage is applied to the piezoelectric element actuator 50 of the dispensing apparatus 100 of the first embodiment and the piezoelectric element actuator 50 of the dispensing apparatus 300 of the third embodiment, the dispensing apparatus 300 of the third embodiment dispenses a smaller amount of liquid as compared with the dispensing apparatus 100 of the first embodiment. Therefore, the dispensing apparatus 300 of the third embodiment is suitable for dispensing a smaller amount of liquid.

2. Dispensing of Cells, Etc.

Figure 12:
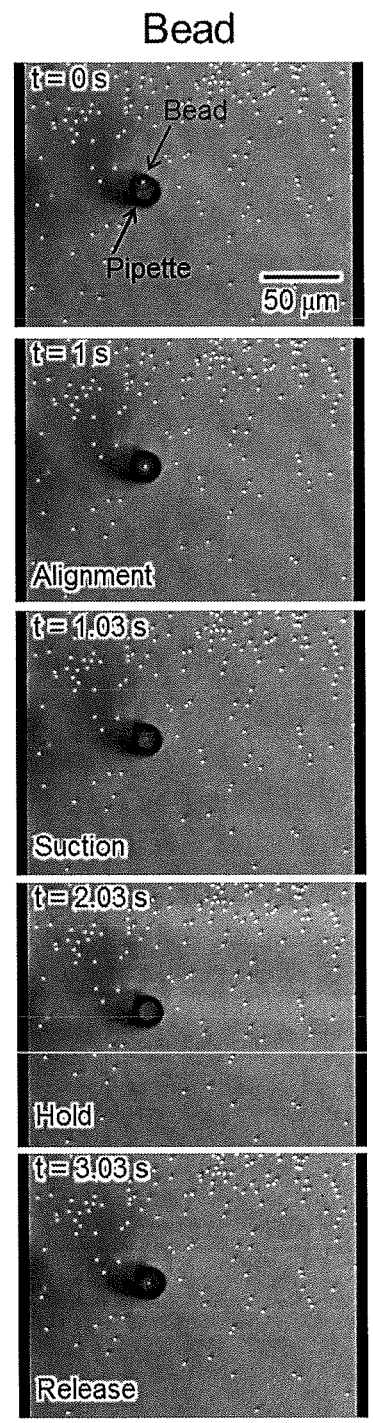
FIG. 12 Sequence of photographs showing the operation steps of the dispensing apparatus of the first embodiment, from collection of a single bead to release of the bead.

Next, an experiment was performed on the operability of the dispensing apparatus 100 of the first embodiment. FIG. 12 is a sequence of photographs showing the operation steps of the dispensing apparatus 100, from collection of a single bead to release of the bead. The diameter of the bead is about 1 μm. As shown in FIG. 12, the dispensing apparatus 100 can collect a single bead with high accuracy without fail. Also, the dispensing apparatus 100 can release the single bead only.

Figure 13:
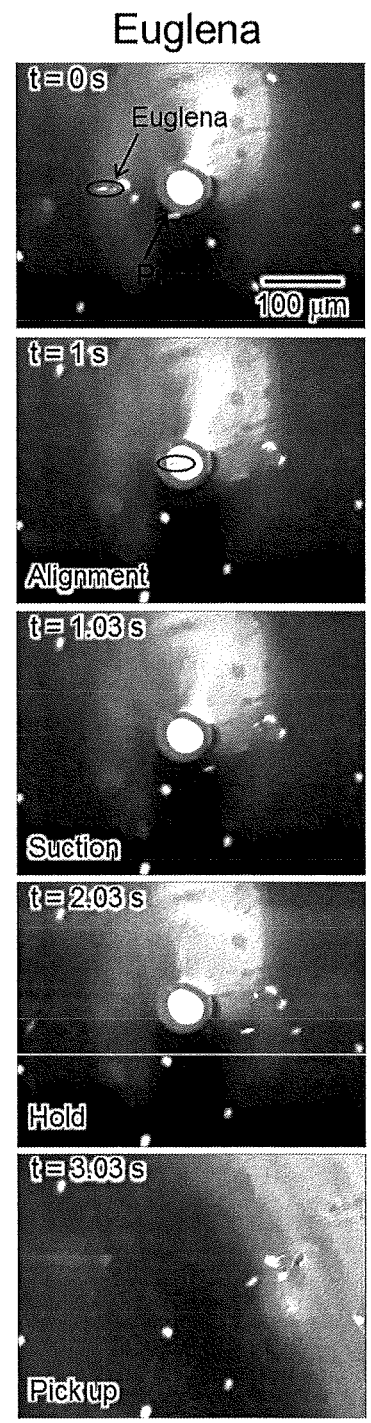
FIG. 13 Sequence of photographs showing the operation steps of the dispensing apparatus of the first embodiment for collecting a single Euglena.

FIG. 13 is a sequence of photographs showing the operation steps of the dispensing apparatus 100 of the first embodiment for collecting a single Euglena. As shown in FIG. 13, the dispensing apparatus 100 can actually collect a single Euglena. Therefore, through use of the dispensing unit described in the modification 3-3, the cells contained in the solution can be dispensed to wells in such a manner that one cell is dispensed to each well.

A. Supplementary Notes

A dispensing apparatus according to a first mode comprises a dispensing spout, a tubular member which is connected to the dispensing spout and which is elastically deformable, and an actuator for compressing the tubular member in an axial direction of the tubular member. The tubular member elastically deforms in the axial direction in its elastically deformable region.

In a dispensing apparatus according to a second mode, the tubular member is a unitary glass member having the dispensing spout.

A dispensing apparatus according to a third mode comprises a dispensing member having the dispensing spout and an opening portion located opposite the dispensing spout. The tubular member is a tubular elastic member having a first open end and a second open end. The first open end of the tubular elastic member is connected to the opening portion of the dispensing member. When the actuator pushes the tubular elastic member from the second open end toward the first open end of the tubular elastic member, the tubular elastic member elastically deforms such that the volume of an internal space of the tubular elastic member decreases.

A dispensing apparatus according to a fourth mode comprises a rod-shaped member connected to an inner wall of the tubular elastic member. The actuator reciprocates the rod-shaped member in an axial direction of the tubular elastic member. A portion of the tubular elastic member located adjacent to the first open end covers a portion of the dispensing member located adjacent to the opening portion. A portion of the tubular elastic member located adjacent to the second open end covers at least a forward end portion of the rod-shaped member.

In a dispensing apparatus according to a fifth mode, when the actuator pushes the rod-shaped member toward the opening portion of the dispensing member, the tubular elastic member elastically deforms such that the cross-sectional area of the internal space of the tubular elastic member decreases.

In a dispensing apparatus according to a sixth mode, the rod-shaped member does not come into contact with the dispensing member during a reciprocating motion of the actuator.

In a dispensing apparatus according to a seventh mode, the outer diameter of the dispensing member on the opening portion side is greater than the inner diameter of the tubular elastic member, and the outer diameter of the forward end portion of the rod-shaped member is greater than the inner diameter of the tubular elastic member.

A dispensing apparatus according to an eighth mode comprises a control unit for controlling an application voltage applied to the actuator. The actuator is a piezoelectric element actuator.

In a dispensing apparatus according to a ninth mode, the control unit controls the application voltage such that a first liquid is held on a side toward the tubular member, a second liquid is held on a side toward the dispensing spout, and a separation bubble is generated between the first liquid and the second liquid.

A dispensing apparatus according to a tenth mode comprises a plate spring. The plate spring is disposed between the actuator and the tubular member.

A liquid dispensing method according to an eleventh mode comprises a first liquid injecting step of injecting a first liquid into an internal space of a dispensing member; a gas injecting step of injecting a gas into the internal space of the dispensing member after the injection of the first liquid; a second liquid injecting step of injecting a second liquid into the internal space of the dispensing member after the injection of the gas; and a releasing step of releasing the second liquid from the dispensing member into a container and releasing a portion of the gas.

A cell dispensing method according to a twelfth mode comprises a first liquid injecting step of injecting a first liquid into an internal space of a dispensing member; a gas injecting step of injecting a gas into the internal space of the dispensing member after the injection of the first liquid; a cell collecting step of injecting a second liquid into the internal space of the dispensing member after the injection of the gas and collecting, one by one, cells contained in the second liquid; and a releasing step of releasing the second liquid and the cells from the dispensing member into a container.

DESCRIPTION OF REFERENCE NUMERALS

100: dispensing apparatus
10: glass pipette
10*a*: dispensing spout
10*b*: opening portion
20: tubular elastic member
20*a*: first open end
20*b*: second open end
30: rod-shaped member
40: plate spring
50: piezoelectric element actuator
60: control unit

The invention claimed is:

1. A dispensing apparatus comprising:
    a dispensing member having a dispensing spout, the dispensing member comprising an opening portion located opposite the dispensing spout;
    a tubular elastic member which is elastically deformable and comprises a first open end, a second open end and a cylindrical space, wherein the opening portion of the dispensing member is inserted and fitted into the first open end of the tubular elastic member;
    a rod-shaped member fitted into the second open end of the tubular elastic member, the rod-shaped member comprising a first end surface and a second end surface; and
    an actuator for compressing the tubular elastic member in an axial direction of the tubular elastic member via the second end surface of the rod-shaped member,
    wherein the tubular elastic member elastically deforms in the axial direction in an elastically deformable region.

2. A dispensing apparatus according to claim 1, wherein when the actuator pushes the tubular elastic member from the second open end toward the first open end of the tubular elastic member, the tubular elastic member elastically deforms such that the volume of an internal space of the tubular elastic member decreases.

3. A dispensing apparatus according to claim 2, wherein the actuator reciprocates the rod-shaped member in an axial direction of the tubular elastic member; and
    a portion of the tubular elastic member located adjacent to the second open end covers at least a forward end portion of the rod-shaped member.

4. A dispensing apparatus according to claim 3, wherein, when the actuator pushes the rod-shaped member toward the opening portion of the dispensing member, the tubular elastic member elastically deforms such that the cross-sectional area of the internal space of the tubular elastic member decreases.

5. A dispensing apparatus according to claim 3, wherein the rod-shaped member does not come into contact with the dispensing member during a reciprocating motion of the actuator.

6. A dispensing apparatus according to claim 1, further comprising a control unit for controlling an application voltage applied to the actuator, wherein the actuator is a piezoelectric element actuator.

7. A dispensing apparatus according to claim 6, wherein the control unit controls the application voltage such that a first liquid is held on a side toward the tubular member, a second liquid is held on a side toward the dispensing spout, and a separation bubble is generated between the first liquid and the second liquid.

8. A dispensing apparatus according to claim 1, further comprising a plate spring, wherein the plate spring is disposed between the actuator and the tubular member.

* * * * *